United States Patent
Moyer

(10) Patent No.: US 9,152,880 B1
(45) Date of Patent: Oct. 6, 2015

(54) METHOD FOR MODELING HUMAN VISUAL DISCRIMINATION TASK PERFORMANCE OF DYNAMIC SCENES

(71) Applicant: The United States of America, as represented by the Secretary of the Army, Washington, DC (US)

(72) Inventor: Steven K. Moyer, Centreville, VA (US)

(73) Assignee: THE UNITED STATES OF AMERICA AS REPRESENTED BY THE SECRETARTY OF THE ARMY, Washington, DC (US)

( * ) Notice: Subject to any disclaimer, the term of this patent is extended or adjusted under 35 U.S.C. 154(b) by 0 days.

(21) Appl. No.: 14/291,055

(22) Filed: May 30, 2014

(51) Int. Cl.
  *G06K 9/46* (2006.01)
  *G06K 9/66* (2006.01)
  *G06K 9/52* (2006.01)
  *G06K 9/62* (2006.01)

(52) U.S. Cl.
  CPC .. *G06K 9/52* (2013.01); *G06K 9/46* (2013.01); *G06K 9/6267* (2013.01)

(58) Field of Classification Search
  CPC ...................................................... G06K 9/52
  See application file for complete search history.

(56) References Cited

U.S. PATENT DOCUMENTS

| | | | |
|---|---|---|---|
| 3,877,011 A * | 4/1975 | Holberg et al. | 342/161 |
| 6,295,367 B1 * | 9/2001 | Crabtree et al. | 382/103 |
| 6,683,968 B1 * | 1/2004 | Pavlovic et al. | 382/103 |
| 7,369,682 B2 | 5/2008 | Yang et al. | |
| 7,650,011 B2 | 1/2010 | Yang et al. | |
| 2006/0239559 A1 * | 10/2006 | Maris | 382/183 |
| 2008/0218402 A1 * | 9/2008 | Matsuura | 342/109 |
| 2010/0067741 A1 * | 3/2010 | Stolkin et al. | 382/103 |

OTHER PUBLICATIONS

"NVESD time-limited search model", Timothy C. Edwards et al., Proceedings of SPIE, vol. 5076, 2003.
"New metric for predicting target acquisition performance" Richard H. Vollmerhausen et al., Optical Engineering, vol. 43(11), pp. 2806-2818, Nov. 2004.

* cited by examiner

*Primary Examiner* — Samir Ahmed
(74) *Attorney, Agent, or Firm* — Richard J. Kim

(57) ABSTRACT

Methods for determining the probability of a human observer correctly performing a visual discrimination task of a target with a dynamic image stream, movie, are based on the $V_{50}$ criterion, or the number of resolvable cycles needed by the human observer for a fifty percent probability of discrimination task completion, for performing the same visual discrimination task of the same targets in static scenes given an infinite amount of time. Once the $V_{50}$ value is determined for the target set using static images, this value is used with the resolvable cycles V of the target set from the movie in an empirical Target Transfer Probability Function TTPF defined by $P_\infty(t) = (V(t)/V_{50}(t))^{1.5}/(1+(V(t)/V_{50}(t))^{1.5})$. The TTPF calculates the probability of correctly performing the visual discrimination task of a target at a given instance in time within the movie. These $P_\infty$ values are then modified by a time limited search equation.

3 Claims, 7 Drawing Sheets

METHOD FOR MODELING HUMAN VISUAL DISCRIMINATION TASK PERFORMANCE OF DYNAMIC SCENES

GOVERNMENT INTEREST

The invention described herein may be manufactured, used, sold, imported, and/or licensed by or for the Government of the United States of America.

FIELD OF THE INVENTION

The present invention applies generally to methods of modeling human performance while using an imaging system. More particularly, the present invention is an analytical method for predicting the performance of humans in classifying and identifying targets while using imaging systems sensitive to the short-, mid-, and long-wave infrared spectral bands as well as monochrome and gray scale visible images.

BACKGROUND OF THE INVENTION

Accurate predictions of a human observer's performance, in terms of not only range at which the human will detect, classify, recognize, or identify a target but also how long it takes to accurately detect, classify, recognize, or identify a target while using electro-optical and forward looking infrared (FLIR) systems are important for several reasons. These predictions are guides for system designers and developers since predictions can be made on theoretical systems prior to manufacture to determine if they are expected to meet performance specifications. The predictions also allow purchasers of systems a way to evaluate manufactured systems for the same purpose. Finally, war game simulations and tactical decision aids use these predictions in order to evaluate engagement tactics. Therefore it is important to accurately model the range and amount of time required for a human to perform a visual discrimination task such as detecting, classifying, recognizing, or identifying a target.

The primary modeling technique for resolution and sensitivity requirements known in the prior art is the Vollmer-hausen Targeting Task Performance (TTP) metric. The TTP metric uses several parameters to accurately model the environment, the imaging system (from entrance optics of the imager through the display), and also incorporates a numerical approximation of Barten's eye Contrast Threshold Function (CTF) to represent the human observer. The TTP metric is then multiplied by the angle subtended to the eye of the target and yields the psychophysical quantity of resolvable cycles (V). These resolvable cycles were used to develop an empirical Target Transfer Probability Function (TTPF). The TTPF then predicts the probability of task completion (detection, classification, recognition, identification) for a particular target or target set at various ranges with some confidence.

The original TTP metric was developed to predict a human observer's ability to detect and identify military vehicles at long ranges, >1 km. At this range, a typical advanced tactical sensor with a 50 µm pixel integrated a space of more than 0.2 m$^2$, which was sufficient when discussing large vehicles, >3 m long. The other assumption of a static scene was also sufficient since most vehicles were either static or moving slowly (in angular velocity) into an attack posture. While this worked well for characterizing human visual discrimination performance for identification of large objects that were either stationary or moving slowly at a large range, it is insufficient for objects moving at moderate speeds and close range or objects which may be rotating and thereby changing their profile to the imaging system. When research into modeling the detection and identification of humans and handheld objects commenced, it became apparent that the tactical range had dramatically shifted from kilometers to hundreds of meters. It is predominately this short range that renders the static observer/static target assumption invalid. An observer moving at only 30 mph will cover a 500 m range in less than 1 minute.

To compensate for this limitation most war gamers assume that a target is static and randomly distributed in aspect to the imaging system and the time to make a higher level visual discrimination decision, such as classification or identification, is assumed to be an instantaneous event. The difficulty of an observer to classify or identify a randomly aspect distributed target is the cycle criterion for the TTPF ($V_{50}$). This $V_{50}$ is the number of resolvable cycles required to correctly detect, classify, recognize, or identify a target with 50 percent probability. This cycle criterion is reported for a number of different target sets but remains as an average over the predefined aspects a target may assume in the environment. In an attempt to determine the $V_{50}$ for either a moving imaging system or a non-stationary target, experiments are being conducted using movies, which has led to an order of magnitude increase in the generation and storage of imagery causing monetary resources to be used for computer memory upgrades. The time to make a higher level visual discrimination decision, such as classification or identification, is usually measured but rarely reported.

The primary technique for modeling the temporal response of a human is known in the prior art as the Edwards-Vollmerhausen Time Limited Search (TLS) model. The TLS model uses the known probability of detection for a target given an infinite amount of time ($P_\infty$) to predict the actual probability of human observers if they do not have an infinite amount of time to search an image or scene. The cumulative probability of finding a target within time t is calculated using an exponential buildup curve equation. The mean time to detect the target is a calibrated parameter which varies due to scene complexity and image quality, but is a function of $P_\infty$. This TLS equation was developed for and strictly applied to the task of detecting targets. Many war gamers assume the task of classifying, recognizing, or identifying targets is an instantaneous event. This assumption could allow for an over prediction in the effectiveness and speed of an engagement involving imaging systems. A human observer may delay in making an identification simply because the target may be moving or turning in hopes of obtaining a better/easier aspect on which to make their decision. This delay in identification affects the temporal speed of a possible engagement and could cascade through an entire war game simulation.

In light of the above, the objectives of the present invention are to provide: a method for predicting the probability of detection, classification, recognition, and identification of either stationary or moving targets with a either a stationary or moving imaging system; a method which can be calibrated from more cost efficient static image experiments; finally a method which can be applied to mono-chrome or gray scale visible spectrum imagery, short-, mid-, and long-wave infrared spectrum imagery.

SUMMARY OF THE INVENTION

Methods for determining the probability of a human observer correctly performing a visual discrimination task of a target with a dynamic image stream, movie, are based on the $V_{50}$ criterion, or the number of resolvable cycles needed by the human observer for a fifty percent probability of discrimination task completion, for performing the same visual discrimination task of the same targets in static scenes given an infinite amount of time. Once the $V_{50}$ value is determined for the target set using static images, this value is used with the resolvable cycles V of the target set from the movie in an empirical Target Transfer Probability Function TTPF defined by $Pc_\infty(t)=(V(t)/V_{50}(t))^{1.5}/(1+(V(t)/V_{50}(t))^{1.5})$. The TTPF calculates the probability of correctly performing the visual discrimination task of a target at a given instance in time within the movie. These $P_\infty$ values are then modified by a time limited search equation.

An exemplary method for modeling human visual discrimination task performance using dynamic scenes in accordance with the present invention includes the step of measuring the number of resolvable cycles $V_a$, for a particular imaging system against a particular target or particular set of targets at a particular range and aspect, as a function of time. The resolvable cycles are given by:

$$V_a(t) = (TTP_a(t))\left(\frac{d_{c,a}(t)}{R(t)}\right)$$

where $d_{c,a}$ is the characteristic size of said target or the average for the set of targets (in meters) and is given by the square root of the cross-sectional area of the target at a particular aspect, R is the range from the imaging system to the target or set of targets (in kilometers), and $TTP_a$ is the number of resolvable cycles per milliradian that an observer with a particular imaging system can achieve given a target's inherent contrast at a particular aspect and atmospheric attenuation between the target and imaging system. These resolvable cycles $V_a$ are then compared to an empirically measured task difficulty parameter $V_{50,a}$, or the number of resolvable cycles required for an observer to achieve a fifty percent (50%) probability of detection, classification, recognition or identification. The Target Transfer Probability Function (TTPF) ratios the number of resolvable cycles V to the number of cycles required for a 50% probability to successfully accomplish the task $V_{50,a}$ and is given by:

$$P_{\infty,a}(t) = \frac{\left(\frac{V_a(t)}{V_{50,a}(t)}\right)^{1.5}}{1+\left(\frac{V_a(t)}{V_{50,a}(t)}\right)^{1.5}}.$$

This $V_{50,a}$ parameter is range independent and its value is governed by the visual discrimination task and items which comprise the target set. In the prior art $V_{50}$ has been based on the targets which make up the target set with multiple aspects of those targets presented to the observer in a human perception experiment. This invention allows both the $V_a$ and $V_{50,a}$ quantities to vary as a function of time. Therefore an aspect dependent $V_{50,a}$ is necessary to account for any turning of the target with respect to the imaging system. However, this aspect dependent $V_{50,a}$ is readily measurable from a static image experiment which contained a sampling of aspects of the targets.

Once the $P_{\infty,a}$ values are calculated, the methods of this invention include the step of scaling them with respect to time by using the Time Limited Search (TLS) equation:

$$P(t) = P_{\infty,a}(t)\left(1 - \exp\left(\frac{-(t-t_d(t))}{\tau(t)}\right)\right),$$

where $t_d$ initially represents the temporal experimental overhead required for an observer to make a response, t is the modeled scenario time, and $\tau$ is the mean time to perform the discrimination task and is given by:

$$\tau(t)=A-B*P_\infty(t)$$

where A and B are empirically determined constants directly measurable from the same static image experiment used to measure the $V_{50,a}$ parameter if the observer response time is also recorded during the experiment. The modeled P(t) value is a cumulative probability versus time. In the prior art, the TLS equation was used strictly for the task of search and detection. In this invention the TLS equation is used for all visual discrimination levels (detection, classification, recognition, and identification) and the mean time to perform a discrimination task $\tau$ is allowed to change as $P_{\infty,a}$ changes temporally. This invention also requires that every instance in which $P_{\infty,a}$ exceeds a threshold value $P_{1,2,3}$, ... a new TLS curve be started by calculating an appropriate $t_d$ factor that is given by:

$$t_d = t + \left(\tau(t)*\ln\left(1 - \frac{P(t-\Delta t)}{P_{\infty,a}(t)}\right)\right) - \Delta t$$

where t is the time of the scenario being modeled and $\Delta t$ is the time increment chosen for the scenario. The results of this invention produce an accurate cumulative probability versus time graph of the scenario being modeled.

BRIEF DESCRIPTION OF THE DRAWINGS

The novel features of this invention will be best understood from the accompanying drawings, taken in conjunction with the accompanying description, in which similar characters refer to similar parts, and in which.

DETAILED DESCRIPTION

By way of background, in prior art a method for modeling human visual discrimination task performance begins with the step of measuring the number of resolvable cycles V, for a particular imaging system against a particular target or particular set of targets at a particular range. The resolvable cycles are given by:

$$V = (TTP)\left(\frac{d_c}{R}\right)$$

where $d_c$ is the characteristic size of said target or the average for the set of targets (in meters) and is given by the square root of the cross-sectional area of the target, R is the distance from the imaging system to the target or set of targets (in kilometers), and TTP is the number of resolvable cycles per milliradian that an observer with a particular imaging system can discriminate given a target's inherent contrast and atmospheric attenuation between the target and imaging system. The Target Transfer Probability Function (TTPF) given by:

$$P_\infty = \frac{\left(\frac{V}{V_{50}}\right)^{1.5}}{1 + \left(\frac{V}{V_{50}}\right)^{1.5}}$$

has been calibrated by measuring the number of resolvable cycles V required for a 50% probability to successfully accomplish the task. This value is then termed the $V_{50}$. Any other modeled value of resolvable cycles can then be ratioed to the $V_{50}$ value and an accurate probability of task performance for an average human observer will then be calculated with the TTPF.

Figure 1:
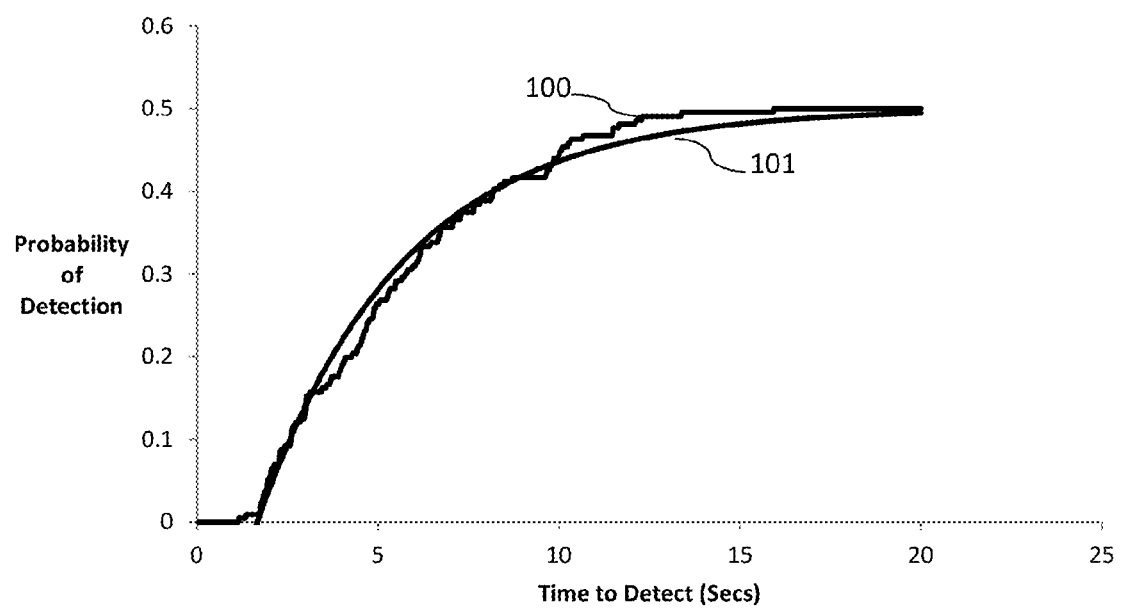
FIG. 1 is a graph of cumulative probability as a function of time both from observer results of a human perception experiment and the Time Limited Search (TLS) model.

For the detection discrimination task, a series of static images, some containing targets and some containing no targets, are presented to the observers and they are asked to locate the region of the image containing the target. The location of their response and the time elapsed from when the image appeared on the screen until they responded are recorded. The responses from the observers are averaged together on an image-by-image basis to calculate the $P_\infty$ value for each image. The resolvable cycles that the target presented in each image is also calculated using a sensor performance metric such as TTP. The sensor performance metric takes into account all imaging sensor physical attributes, environmental conditions, existing external lighting conditions, characteristic size of target, target signature, and range to target. The $V_{50}$ parameter that maps the calculated resolvable cycles closest to the observer $P_\infty$ values is the measured $V_{50}$ for the detection task of the set of targets which were detected. The recorded observer response time for each image is then compiled for all images which contain a similar observer $P_\infty$ value. The contribution to the total probability of detection of each correct response, s, is normalized, such that $P_s = P_\infty *(1/S)$, where S is the total number of observer responses. The summed probability as a function of response time is shown in FIG. 1, 100.

Figure 2:
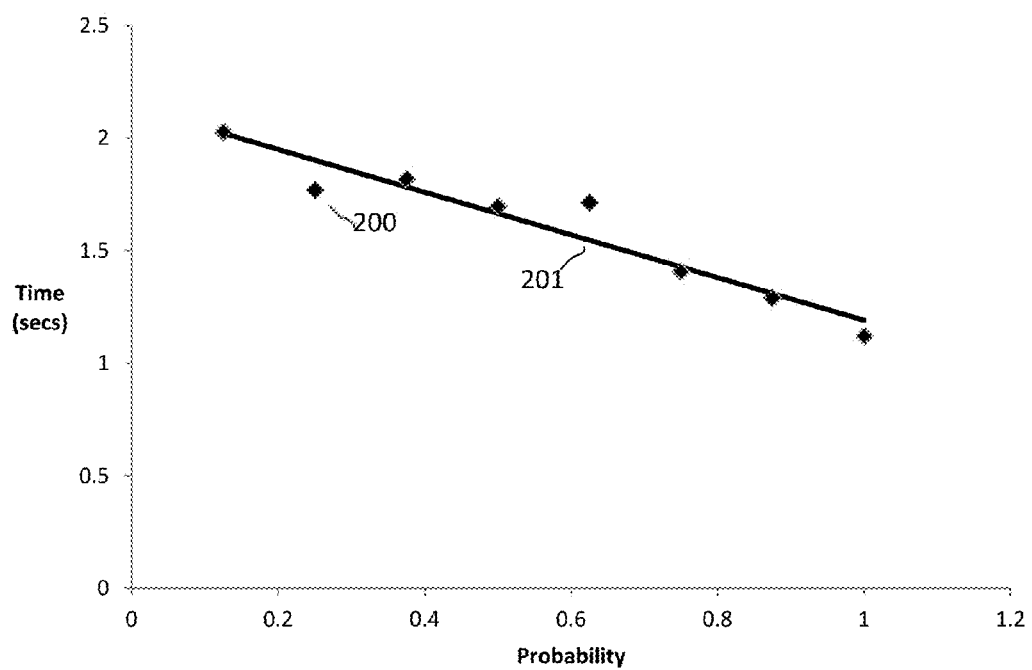
FIG. 2 is a graph of the mean time to detect a target as a function of probability given infinite time.

The TLS equation is given by:

$$P(t) = P_\infty\left(1 - \exp\left(\frac{-(t - t_d)}{\tau}\right)\right)$$

where $t_d$ represents the temporal experimental delay required for an observer to record a response, t is the elapsed time in the experiment to achieve a measured probability value, and τ is the mean time to perform the discrimination task. The resulting model is indicated by 101 in FIG. 1. Once all images have been grouped by $P_\infty$ and the mean time to detect the target determined, a relationship between the mean time to detect and the $P_\infty$ value may be measured usually given by:

$$\tau = A - B * P_\infty$$

where A and B are empirically determined constants. Shown in FIG. 2 are the measured mean time to detect a target at specified $P_\infty$ values 200 and the continuous model that relates all $P_\infty$ values to their respective mean times to detect, 201.

For higher order discrimination tasks (classification, recognition, and identification), an N-alternative forced choice experiment with single frame static images of a set of targets is conducted. The set of targets are chosen to be consistent with the definition of the discrimination task being measured and the targets are generally shown at multiple aspects. The target set is generally degraded in discrete steps in either resolution or sensitivity. When presented with a degraded target image, the observer is given N-alternatives to choose from in making their response. The correctness of their responses and the elapsed time from when the image appeared on the screen until they responded are recorded. An individual observer's responses are then averaged across all targets and aspects by resolution/sensitivity level and then an average is taken of all observers for each resolution/sensitivity level. This produces a measured average observer probability value for the target set at each experimental level. By the nature of the forced choice experimental set-up, a potentially significant probability of correct responses could be achieved by guessing. A method to remove the probability of guessing is given by:

$$P_\infty = \frac{P_M - (1/N)}{1 - (1/N)}$$

where $P_M$ is the observer probability measured in the experiment and N is the number of alternatives in the experiment. Unlike the detection task, an average number of resolvable cycles is measured for each discrete level of degradation or experimental cell using a sensor performance metric such as TTP. This is accomplished by averaging over the target sets characteristic size and averaging the target sets contrast together. The $V_{50}$ parameter that maps the calculated resolvable cycles closest to the corrected $P_\infty$ values is the measured $V_{50}$ for the discrimination task of the set of targets. Once the $V_{50}$ value is determined for a discrimination task and target set, the imaging system parameters may be changed, different atmospheric conditions may be assumed, even ranges changed and the human performance modeling will be an accurate representation of an actual observer with an imaging system in that environment, if both the targets and observer are in a static or near static condition.

The above cited processes are well known in the art and are further described in the open literature specifically in "NVESD time-limited search model", Timothy C. Edwards et al., Proceedings of SPIE, vol. 5076, 2003, and "New metric for predicting target acquisition performance" Richard H.

Vollmerhausen et al., Optical Engineering, vol. 43(11), pp. 2806-2818, which are hereby incorporated by reference. The Targeting Task Performance (TTP) metric can be used for detection, classification, recognition and identification tasks if only the probability of human performance is required, but must be coupled with the Time Limited Search (TLS) equation to gain the added in sight to the time it takes an observer to make a detection.

Methods are disclosed for determining the probability of a human observer correctly performing a visual discrimination task (detection, classification, recognition, or identification) of a target with a dynamic image stream, movie, based on the $V_{50}$ criterion, or the number of resolvable cycles needed by the human observer for a fifty percent probability of discrimination task completion, for performing the same visual discrimination task of the same targets in static scenes given an infinite amount of time. Once the $V_{50}$ value is determined for the target set using static images, this value is used with the resolvable cycles (V) of the target set from the movie in an empirical Target Transfer Probability Function (TTPF) defined by $P_\infty(t)=(V(t)/V_{50}(t))^{1.5}/(1+(V(t)/V_{50}(t))^{1.5})$. The TTPF calculates the probability of correctly performing the visual discrimination task of a target at a given instance in time within the movie. These $P_\infty$ values are then modified by the time limited search (TLS) equation $P(t)=P_\infty(t)(1-\exp(-(t-t_d)))$ where t is the actual time in the movie in seconds, $t_d$ is the experimental time delay associated with experimental set up, and $\tau(t)$ is the mean time to perform the visual discrimination task, and is calculated as $\tau(t)=A-B*P_\infty(t)$. A and B are calibration constants that are measured from a static image perception experiment and encompass the target set and a representative clutter level of the movie.

Exemplary methods of the present invention are described in greater detail. For example, an exemplary method for predicting a human observers probability of detection, classification, recognition, and identification of either stationary or moving targets with either a stationary or moving imaging system comprises the steps of:

Step A: Measuring an aspect varying $V_{50,a}$ as the cycle criterion required for a fifty percent (50%) probability of detection, classification, recognition, or identification of a particular target set imaged within a specific spectral region for each target set at each specified aspect through the conduct of a human perception experiment, either N-alternative forced choice experiment, or free response, using images of static targets from static imaging systems measuring simultaneously observer response to the visual discrimination task under investigation and the time required for that response;

Step B: Measuring the mean time to accomplish a visual discrimination task (τ) as a function of the probability of accomplishing the visual discrimination task through the conduct of a human perception experiment, either N-alternative forced choice experiment, or free response, using images of static targets from static imaging systems measuring simultaneously observer response to the visual discrimination task under investigation and the time required for that response;

Step C: Determining the cycles resolved ($V_a$) on a target set for a specific sensor as the number of equivalent cycles resolved by the sensor temporally according to the relationship:

$$V_a(t) = TTP_a(t)\left(\frac{d_{c,a}(t)}{R(t)}\right);$$

Step D: Determining the probability, $P_{\infty,a}$, of visual task performance according to the relationship:

$$P_{\infty,a}(t) = \frac{\left(\frac{V_a(t)}{V_{50,a}(t)}\right)^{1.5}}{1+\left(\frac{V_a(t)}{V_{50,a}(t)}\right)^{1.5}};$$

Step E: Determining the mean time to accomplish a visual discrimination task (τ);

Step F: Determining if cumulative probability has exceeded a threshold and requires a new cumulative probability function needs to be started by calculating an updated time delay ($t_d$); and Step G: Calculating an accurate probability of human observer performance as a function of time for output in predicting a human observers probability of detection, classification, recognition, and/or identification of either stationary or moving targets.

Figure 3A:
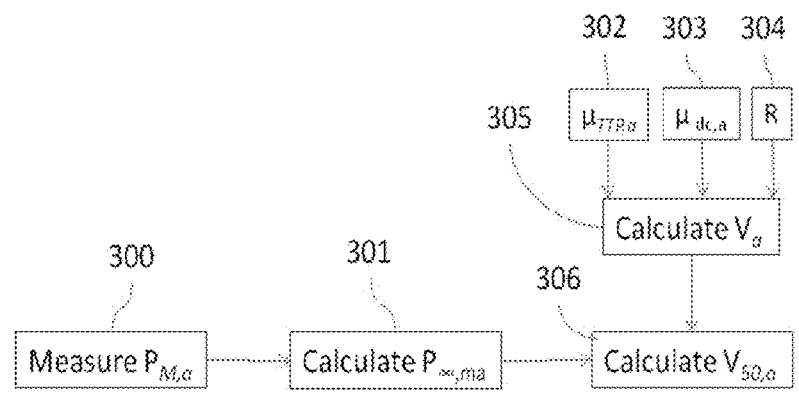
FIG. 3a is an exemplary block diagram that illustrates the steps of an exemplary method to calibrate the present invention in resolution, sensitivity and temporally.
Figure 3B:
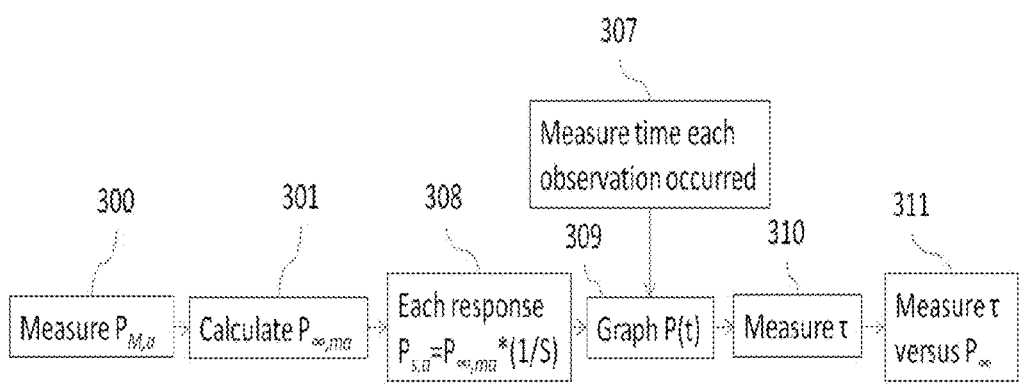
FIG. 3b is another exemplary block diagram that illustrates alternative steps to a method to calibrate the present invention in resolution, sensitivity and temporally.

Referring now to FIGS. 3a and 3b, an exemplary analysis methodology required to produce an accurate model calibration for the present invention in resolution, sensitivity, and temporally is disclosed. For calibration purposes, a standard static image static imaging system human perception experiment is conducted, as is already known in the art for all levels of human observer visual discrimination. In order to calibrate the present invention for resolution and sensitivity, either an N-alternative forced choice experiment, or free response experiment, is conducted with single frame static images. Each image contains a single target however the set of images span a set of targets at different aspects. However, unlike the present art, the observers' probabilities must be calculated for the set of targets at each aspect as depicted by block 300 in FIGS. 3a and 3b. The probabilities for an N-alternative forced choice experiment are then adjusted to remove the probability that the observer guessed correctly according to the relationship:

$$P_{\infty,ma} = \frac{P_{M,a}-(1/N)}{1-(1/N)}$$

where $P_{M,a}$ is the probability measured from the observers and N is the number of alternatives in the N-alternative forced choice experiment for each target set aspect, depicted in block 301. If an N-alternative forced choice experiment is not used, then no correction of probability is needed. Turning now to FIG. 3a, the average number of resolvable cycles the observers were presented is then calculated for the set of targets at each aspect, according to the relationship:

$$V_a = (\mu_{TTP,a})\left(\frac{\mu_{d_c,a}}{R}\right)$$

where $\mu_{TTP,a}$ is the average number of resolvable cycles per milliradian for each experimental cell, depicted in block 302, $\mu_{dc,a}$ is the average characteristic size of said target or the average for the set of targets (in meters) and is given by the square root of the cross-sectional area of the target at a particular aspect, depicted in block 303, and R is the distance from the imaging system to the target or set of targets (in kilometers), depicted in block 304. These resolvable cycle values, depicted in block 305, are correlated to the measured $P_{\infty,ma}$ values through the TTPF, given by:

$$P_{\infty,a} = \frac{\left(\frac{V_a}{V_{50,a}}\right)^{1.5}}{1+\left(\frac{V_a}{V_{50,a}}\right)^{1.5}}$$

where $V_{50,a}$ is the fit parameter for the TTPF, depicted in block 306. The value of $V_{50,a}$ that allows the $P_{\infty,a}$ value to most closely match the measured $P_{\infty,ma}$ values is the correct $V_{50,a}$ value. This then establishes the resolution and sensitivity requirements to perform the visual discrimination task for the target set at each of the target aspects tested for in the current invention.

Turning specifically to FIG. 3b, in order to calibrate the current invention for temporal distribution for all visual discrimination levels, the current invention requires measurement of the amount of time each observer requires to make a correct discrimination, as depicted in block 307. Each correct response is weighted to have a $P_{s,a=P\infty,ma}*(1/S)$ value, where S is the total number of observer responses as depicted in block 308. These individual responses are graphed as probability versus time and will be a cumulative probability build-up curve, as depicted in block 309, will be similar to the one shown in FIG. 1, 100. Referring to FIG. 3b, the mean time to detect is a fit parameter for the TLS equation given by:

$$P(t) = P_{\infty,ma}\left(1-\exp\left(\frac{-(t-t_d)}{\tau}\right)\right)$$

where $t_d$ represents the temporal experimental overhead required for an observer to make a response, and $\tau$ is the mean time to perform the discrimination task, as depicted in block 310. Once all images in each experimental cell have been grouped and the mean time to detect the target determined, a relationship between the mean time to detect and the $P_\infty$ value may be measured usually given by:

$$\tau = A - B*P_{\infty,ma}$$

where A and B are empirically determined constants, as depicted in block 311. This yields a continuous model that relates all $P_{\infty,ma}$ values to their respective mean times to detect.

Figure 4:
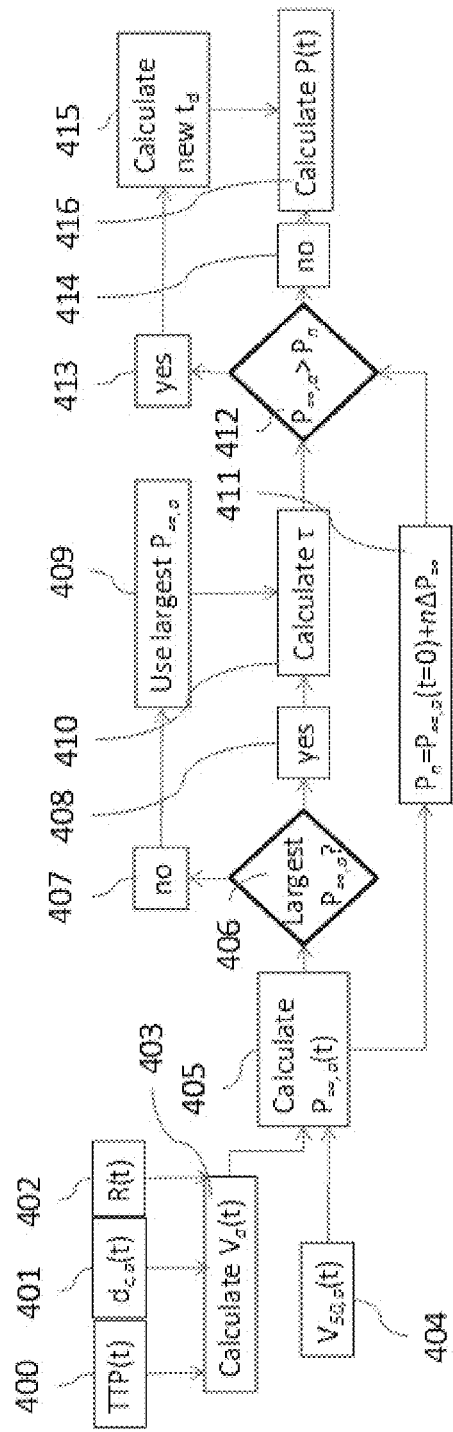
FIG. 4 is a block diagram that illustrates the steps of the methods of the present invention.

Once the $\tau$ versus $P_{\infty,ma}$ relationship is modeled and the resolution and sensitivity requirement measured for the target set and for the visual discrimination task, the current invention is considered calibrated. Referring to FIG. 4 of the current invention, the imaging system and environmental conditions are modeled using the TTP metric, as depicted in block 400. If the environmental conditions can be considered unchanging with respect to the time scale of the scenario, the imaging system only needs to be modeled once with the present environmental conditions; otherwise the TTP must be modeled as a function of time. The characteristic size, $d_{c,a}$, of the target set needs to be known temporally, as depicted in block 401, as well as the range, R, from the imaging system to the target set as a function of time, as depicted in block 402. The resolvable cycles as a function of time can then be calculated given by:

$$V_a(t) = (TTP(t))\left(\frac{d_{c,a}(t)}{R(t)}\right).$$

A scenario to be modeled is generated with accurate values of the number of resolvable cycles an observer would experience as a function of time, depicted in block 403. This scenario also requires an accurate description of the target aspect to the imaging system as a function of time, as depicted in block 404. The $P_{\infty,a}$ value as a function of time will then be calculated using a time dependent TTPF given by:

$$P_{\infty,a}(t) = \frac{\left(\frac{V_a(t)}{V_{50,a}(t)}\right)^{1.5}}{1+\left(\frac{V_a(t)}{V_{50,a}(t)}\right)^{1.5}}$$

as depicted in block 405. As the scenario evolves in time the current invention uses the largest $P_{\infty,a}$ value, up to the current time, in calculating the mean time to accomplish the visual discrimination task. This decision is depicted in block 406. If the current time $P_{\infty,a}$ value is less than the largest $P_{\infty,a}$ value until that time then, depicted in block 407, then the largest previous $P_{\infty,a}$ value is used, depicted in block 409, in calculating the mean time to accomplish the visual discrimination task ($\tau$) depicted in block 410 and given by:

$$\tau(t) = A - B*P_{\infty,a}(t)$$

where A and B were previously calibrated coefficients for the discrimination task and target set. If the current time $P_{\infty,a}$ value is larger than all previous time $P_{\infty,a}$ values, depicted in block 408, than $\tau(t)$ is directly calculated using this current $P_{\infty,a}$ value, as depicted in block 410.

A series of threshold values, $P_n$, are established with the calculation of the initial $P_{\infty,a}$ value and is given by:

$$P_n = P_{\infty,a}(t=0) + n\Delta P_\infty$$

where n starts at zero and increases in integer increments to infinity and $\Delta P_\infty$ has a magnitude of $\Delta t/25$ with $\Delta t$ being the time increment of the simulation, as depicted in block 411. The factor of 25 in $\Delta P_\infty$ that determines the threshold values for starting a new probability is a minimum value that provides good agreement to experimental data. The next decision, depicted in block 412, is if the current $P_{\infty,a}$ value is greater than $P_1$ initially. If the current $P_{\infty,a}$ value is less than the $P_1$, as depicted by block 414, than P(t) is calculated, as depicted in block 416, given by:

$$P(t) = P_{\infty,a}(t)\left(1-\exp\left(\frac{-(t-t_d)}{\tau(t)}\right)\right)$$

where $t_d$ initially is the amount of time associated with the observers taking some action due to their decision, such as highlighting a region on a display or vocalizing the target present. If the current $P_{\infty,a}(t)$ value has just exceeded a threshold $P_n$ value, as depicted in block 412, a new threshold value is established $P_{n+1}$, and a new $t_d$ needs to be calculated in order to start a new cumulative probability curve, as depicted by block 415. This accomplished according to the relationship:

$$t_d = t + \left(\tau(t) * \ln\left(1 - \frac{P(t-\Delta t)}{P_{\infty,a}(t)}\right)\right) - \Delta t$$

where $\tau(t)$ and $P_{\infty,a}(t)$ are current time values, $P(t-\Delta t)$ is the previous time value of $P(t)$, $\Delta t$ is the time increment used in the simulation. This new value of $t_d$ is used to calculate $P(t)$, as depicted in block 416, in all subsequent time steps until the $P_{\infty,a}$ value exceeds the next threshold value $P_{n+1}$. Since the largest $P_{\infty,a}$ value is used, $P_{\infty,a}$ can never decrease and threshold values can only be exceeded once. This cycle of periodically starting new cumulative probability curves continues until $P_{\infty,a}$ values no longer exceed the next higher threshold value. However $\tau(t)$ is allowed to change as long as $P_{\infty,a}(t)$ values increase until $P_{\infty,a}$ reaches a global maximum. The global maximum $P_{\infty,a}$ value is then used for the remainder of the scenario being modeled.

The current invention was tested with three human perception experiments, a search and detection experiment from a moving vehicle, a target recognition experiment where the target was turning with respect to the imaging system and the imaging system was stationary, and a target identification experiment where the target was turning with respect to the imaging system and the imaging system was stationary. All human observers were unique to each experiment. However, each human observer participated in both the static image calibration experiments and the dynamic image experiments. The current invention modeled the observer results at a temporal frequency of 30 Hz.

Figure 5:
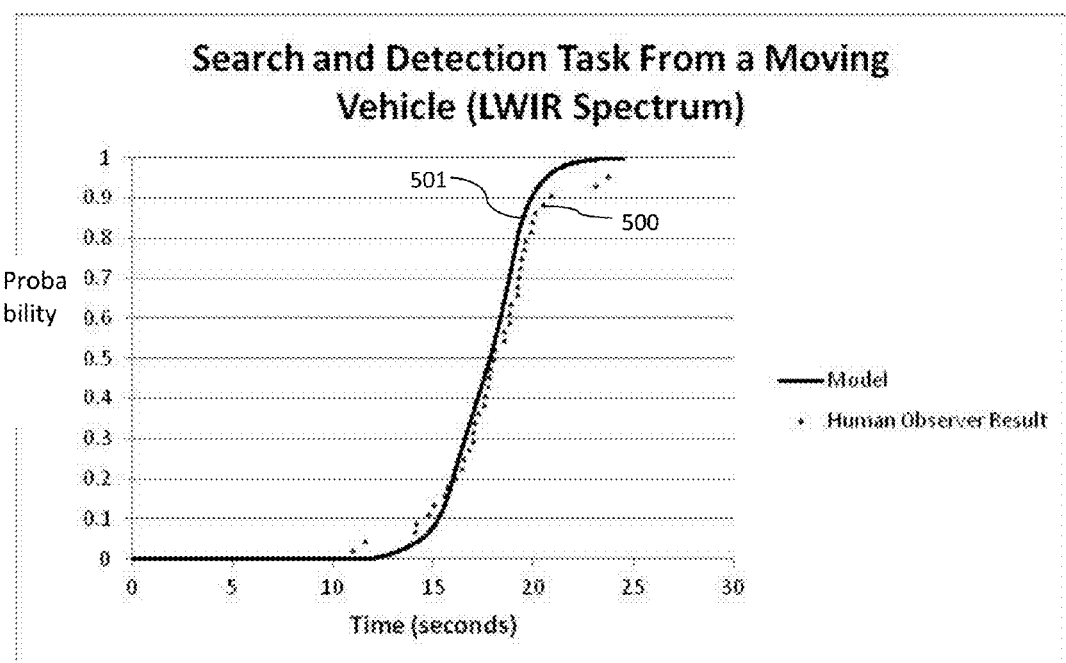
FIG. 5 is a graph of cumulative probability as a function of time showing both human observers performing the task of target detection with a long-wave infrared (LWIR) imaging system from a moving vehicle and the prediction of the present invention (model).
Figure 6:
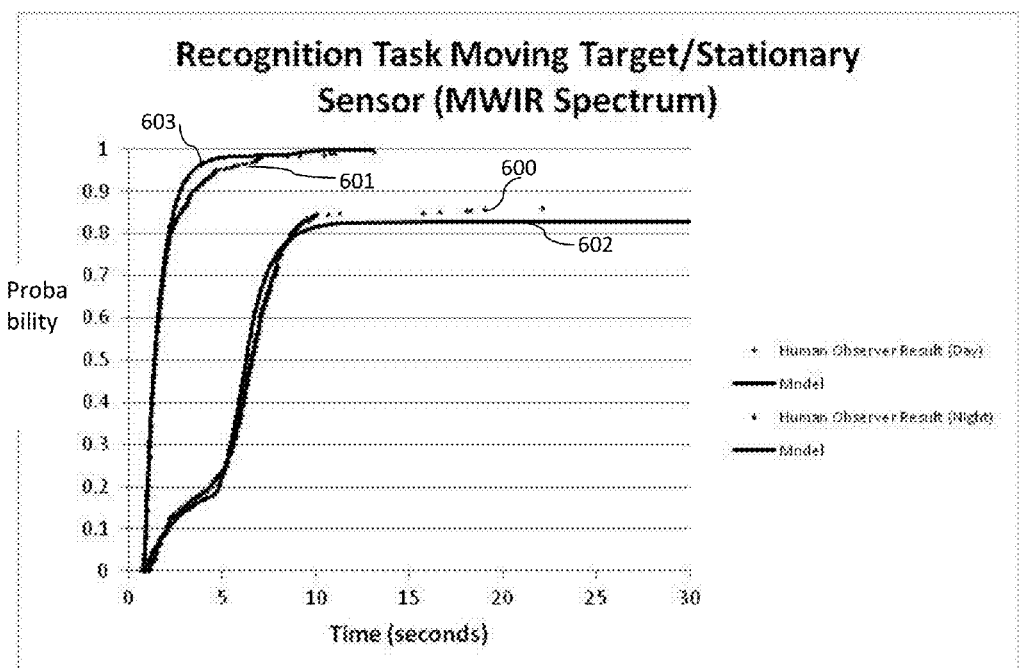
FIG. 6 is a graph of cumulative probability as a function of time showing both human observers performing the task of target recognition with a mid-wave infrared (MWIR) imaging system, while the target is moving and the imaging system is stationary, and the prediction of the present invention (model).
Figure 7:
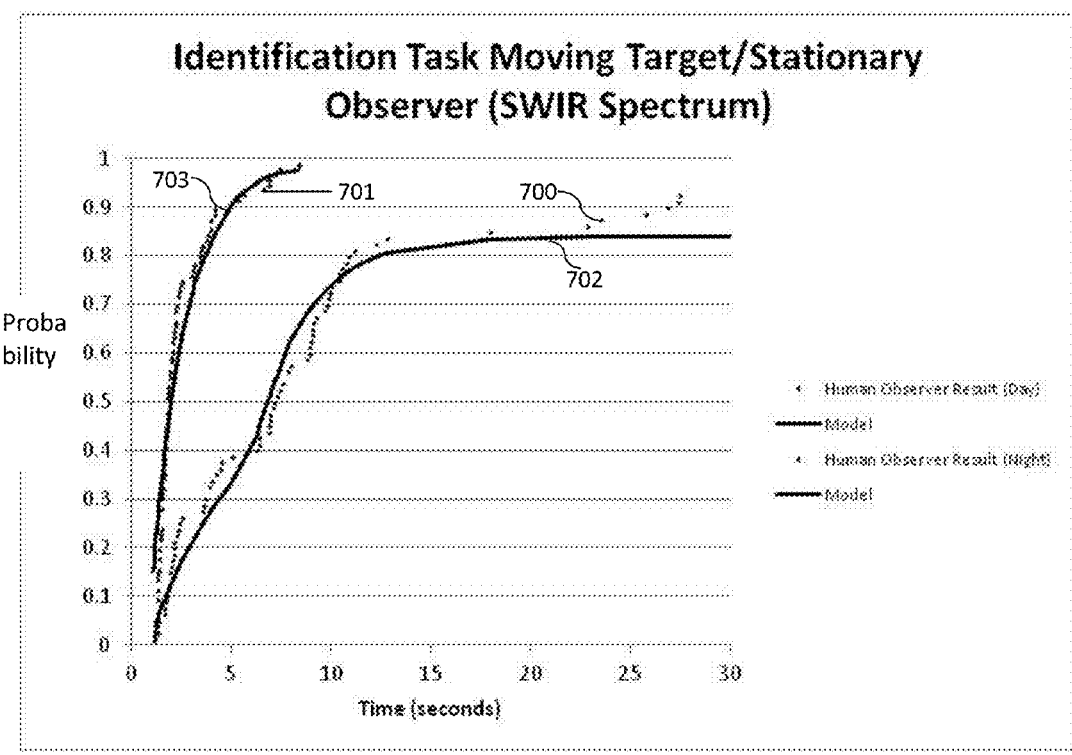
FIG. 7 is a graph of cumulative probability as a function of time showing both human observers performing the task of target identification with a short-wave infrared (SWIR) imaging system, while the target is moving and the imaging system is stationary, and the prediction of the present invention (model).

FIGS. 5, 6, and 7 show results of the experiments and the current invention predictions for these human visual perception tasks, spectral waveband, and time of day. The graphs labeled 500, 600, 601, 700, and 701 show the cumulative probability of the human observers as they viewed the dynamic scenes. Graphs 501, 602, 603, 702, and 703 show the predictions of the current invention to these dynamic scenes after calibration to a static scene human perception experiment for each task, spectral waveband, and time of day. These graphs clearly show the advantages of the present invention to predict human observer visual discrimination task performance in a variety of spectral wavebands and different times of day.

Those of skill in the art will appreciate still additional alternative structural and functional designs for a human observer predictive model by differentiating the current embodiment with respect to time and their applications through the disclosed principles of the present invention. Thus, while particular embodiments and applications of the present invention have been illustrated and described, it is to be understood that the invention is not limited to the precise construction and components disclosed herein and that various modifications, change and variations which will be apparent to those skilled in the art may be made in the arrangement, operation and details of the method and apparatus of the present invention disclosed herein without departing from the spirit and scope of the invention as defined in the appended claims.

What is claimed is:

1. A method for determining the probability of a human observer correctly performing a visual discrimination task based on a visual display of a dynamic image stream or movie, comprising: an imaging system configured to
    determine a number of resolvable cycles needed by the human observer for a fifty percent probability of discrimination task completion as a $V_{50}$ value given a set of targets in a static image perception experiment;
    use the determined $V_{50}$ value with a resolvable cycles value V of the target set from the movie in an empirical target transfer probability function to calculate probability values $P_\infty$ of correctly performing the visual discrimination task of a target at a given instance in time within the movie, wherein the visual discrimination task is based on the number of resolvable cycles needed by the human observer for a fifty percent probability of discrimination task completion for performing the same visual discrimination task of the same targets in the static image given an infinite amount of time;
    measure calibration constants A and B from the static image perception experiment and encompassing the target set and clutter level of the movie;
    modify the $P_\infty$ values by a time limited search equation based on an actual time in the movie in seconds, an experimental time delay associated with experimental set up, and a mean time to perform the visual discrimination task, wherein the mean time to perform the visual discrimination task is based on the $P_\infty$ values and the measured calibration constants A and B; and
    determining the probability of a human observer correctly performing a visual discrimination task based on the modified P∞.

2. The method according to claim 1, wherein the empirical target transfer probability function is defined by $P_\infty(t)=(V(t)/V_{50}(t))^{1.5}/(1+(V(t)/V_{50}(t))^{1.5})$.

3. The method according to claim 1, wherein the time limited search equation for modifying the $P_\infty$ values is defined by $P(t)=P_\infty(t)(1-\exp(-(t-t_d)/\tau(t)))$ where t is the actual time in the movie in seconds, to is the experimental time delay associated with experimental set up, and $\tau(t)$ is the mean time to perform the visual discrimination task, and is calculated as $\tau(t)=A-B*P_\infty(t)$.

* * * * *